United States Patent [19]

Szejtli et al.

[11] 4,380,626

[45] Apr. 19, 1983

[54] HORMONAL PLANT GROWTH REGULATOR

[75] Inventors: Jozsef Szejtli; Zsuzsanna Budai; Magda Tetenyi nee Erdosi; Gabriella Pap nee Imrenyi, all of Budapest, Hungary

[73] Assignee: Chinoin Gyogyszer es Vegyeszeti Termekek Gyara R.T., Budapest, Hungary

[21] Appl. No.: 218,206

[22] Filed: Dec. 19, 1980

[30] Foreign Application Priority Data

Dec. 28, 1979 [HU] Hungary .............................. CI 2000

[51] Int. Cl.³ ............................................. C08B 37/16
[52] U.S. Cl. ....................................... 536/103; 71/71; 71/86; 71/88; 106/210; 106/213
[58] Field of Search .................... 106/210, 213; 71/71, 71/86, 88; 536/103

[56] References Cited

U.S. PATENT DOCUMENTS

| | | | |
|---|---|---|---|
| 3,420,788 | 1/1969 | Solms | 536/103 |
| 3,426,011 | 2/1969 | Parmerter et al. | 536/103 |
| 3,728,381 | 4/1973 | Randall et al. | 71/86 |
| 3,960,540 | 6/1976 | Crosby | 71/86 |
| 4,152,429 | 5/1979 | Hayakawa et al. | 71/86 |
| 4,228,160 | 10/1980 | Szejtli et al. | 536/103 |
| 4,240,819 | 12/1980 | Fritz et al. | 71/86 |

FOREIGN PATENT DOCUMENTS

2037306 7/1980 United Kingdom .
2061987 5/1981 United Kingdom .

OTHER PUBLICATIONS

Chemical Abstracts, vol. 93, No. 9, Sep. 1, 1980, item 90575p.
Chemical Abstracts, vol. 93, No. 22, Dec. 1, 1980, item 210272m.
Chemical Abstracts, vol. 93, No. 26, Dec. 29, 1980, item 241519b.

*Primary Examiner*—Ronald W. Griffin
*Attorney, Agent, or Firm*—Karl F. Ross; Herbert Dubno

[57] ABSTRACT

The present invention relates to new inclusion complexes of 2-chloro ethyl phosphonic acid formed with α-, β- and/or γ-cyclodextrin or a mixture thereof.

The new inclusion complexes contain preferably 10–30% of 2-chloro ethyl phosphonic acid.

The new complexes of the present invention are prepared by reacting 2-chloro ethyl phosphonic acid with α-, β- and/or γ-cyclodextrin or a mixture of one or more of the said cyclodextrins and linear dextrins and/or partially decomposed starch.

The new inclusion complexes of the present invention can be used for the preparation of plant growth regulating compositions.

10 Claims, No Drawings

HORMONAL PLANT GROWTH REGULATOR

FIELD OF THE INVENTION

This invention relates to a composition having hormonal activity, a process for the preparation of the active ingredient and a method for the regulation of plant growth.

The plant growth regulating compositions comprise as active ingredient an inclusion complex of α-, β- and/or γ-cyclodextrin formed with chloroethyl-phosphonic acid.

BACKGROUND OF THE INVENTION

Ethylene belongs to the group of plant hormones of natural origin. In a concentration of 0.02–1 ppm ethylene is capable of inhibiting the growth of the stem, exerting defoliant effect and accelerating the ripening of fruits [OSBORNE, J. Plant Growth Regulators, S.C.I. Monograph No. 31 p. 236, (1968)].

The use of gaseous ethylene is accompanied by a number of technical difficulties and consequently has been limited in practice. The preparation of the complex of ethylene and α-cyclodextrin was described by CRAMER and HENGLEIN in 1957 [Chem. Ber. 90, 2572 (1957)].

A complex of 0.7 mole of ethylene per 1 mole of α-cyclodextrin is known from the prior art (KOKAI No. 75 58226); according to this patent application the use of the complex results in the shortening of the ripening period of the tomato by about 4 days. Since the complex contains about 0.7 mole of ethylene per 1 mole of cyclodextrin and the percentage ethylene content of the complex is only 2% the complex is only of theoretical value and be used in practice in this form.

In practice when ethylene activity is required compounds are used from which, on decomposition, ethylene is evolved on the surface of the plant or in the interior of the cells. 2-chloroethylphosphonic acid is such a compound of the most widespread application.

On decomposition of 2-chloroethylphosphonic acid with water, hydrochloric acid, phosphoric acid and gaseous ethylene are evolved. Decomposition takes place only at a pH value above 3.5. The commercial products are mixtures which contain various by-products and water. The most frequently used composition is an aqueous solution comprising approximately 40% of 2-chloroethylphosphonic acid.

When sprayed onto the plants in a suitable dilution 2-chloroethylphosphonic acid enhances the intensity of respiration, increases the activity of chlorophyllase and thus decreases the chlorophyll content of the leaves and exerts defoliating activity.

The pH value of the commercially available 2-chloroethylphosphonic acid concentrates is about 2 in order to inhibit the decomposition of the compound. This low pH value is not advantageous from the point of view of application (corrosion) nor is it advantageous for the reason that the 2-chloroethylphosphonic acid penetrating the plant does not exert a local effect only, but on absorption due to the systemic effect the activity can be observed in the following year and it damages the buds.

DESCRIPTION OF THE INVENTION

The present invention is based on the recognition that 2-chloroethylphosphonic acid forms crystalline inclusion complexes with cyclodextrins which can be stored in powder form without any restrictions and are to be dissolved just before spraying. The inclusion complexes of the present invention can be used as dusting powders as well. In this case the crystalline complex form provides a prolonged effect.

The 2-chloroethylphosphonic acid content of the inclusion complexes of the present invention is from 10 to 30%.

The 2-chloroethylphosphonic acid is referred to as "ethrel" throughout the remainder of the specification.

The ethrel-cyclodextrin complexes of the present invention differ from the hitherto known ethylenecyclodextrin complex not only in the higher ethylene content. The fundamental difference resides in the fact that the ethrel-cyclodextrin complex exhibits its effect in a biological way; the complex when applied on the surface of the living plant penetrates and translocates in the tissues and organs of the plant and the gaseous ethylene—which actually exerts the growth regulating hormonic activity—is evolved at the pH of the cells. The known ethylenecyclodextrin complex stimulates the ripening of gathered unripe tomato and banana by setting free ethylene in a closed area in the course of decomposition. This ethylene formation is extremely rapid; very high local ethylene concentrations and large losses occur. On the other hand ethylene is set free from the ethrel-cyclodextrin complex of the present invention in at least two steps (at first the ethrel-cyclodextrin complex releases the ethrel and thereafter the ethrel liberates ethylene). The latter step ensures release retardation and also a long-lasting ethylene effect which is important in terms of the biological response reaction. The field of application of the ethrel-cyclodextrin complex is not limited to the stimulation of ripening during storage (the formation of a closed storing area with high ethylene content) but it can be used for various objects (e.g. the regulation of the complete flowering-blossoming and crop-forming mechanism of the living growing plant) by appropriate selection of the mode and period of time of application and the goal.

According to the present invention there is provided a process for the preparation of an inclusion complex of 2-chloroethylphosphonic acid and cyclodextrin. The said process comprises the reaction of 2-chloroethylphosphonic acid with α-, β- and/or γ-cyclodextrin or a mixture of one or more of the cyclodextrins formed with a linear dextrin and/or partially decomposed starch.

Preferably the method comprises adding to cyclodextrins or a mixture of cyclodextrins and linear dextrins or an aqueous solution thereof a solution of 2-chlorethylphosphonic acid formed with water or a mixture of water and a water-miscible organic solvent. As the solvent preferably lower alcohols and ketones can be used.

Further details of the present invention are illustrated by the following Examples without limiting the scope of protection to the said Examples.

EXAMPLE 1

Process for the preparation of a complex of α-cyclodextrin and 2-chloroethylphosphonic acid A 50% aqueous solution of α-cyclodextrin is prepared in distilled water under warming (70°–80° C.). A 40% solution of chloroethylphosphonic acid (Rol-Fruct, Chinoin product) of equal volume is added under vigorous stirring. The solution thus obtained is cooled with icecold water under further stirring and the reaction mixture is allowed to stand in a refrigerator overnight. The precipitated small crystals are filtered off and dried in a vacuum desiccator over potassium hydroxide for two days. The dry product thus obtained is of a weak greenish shade, readily pulverizable, white in powdered form and consists of small powderlike crystals. Yield: 104% (related to the amount of the introduced α-cyclodextrin). The product is a complex of α-cyclodextrin and chloroethylphosphonic acid.

Free chloride ion content: 0% (according to Volhard).
Fixed chloride content: 7.03% (after heating to boiling with a 1 N potassium hydroxide solution for an hour; according to Volhard).
7.03% of Cl→5.55% of ethylene→28.6% of 2-chloroethylphosphonic acid→2.7 moles/mole of α-cyclodextrin.

On the basis of the ethylene content:
The amount of the evolved gaseous ethylene is determined by means of reaction kinetic measurings with the aid of a Warburg apparatus. The average result of the repeated measurements is 745 μl of ethylene per 20 mg. of complex.
745 μl of ethylene/20 mg. of complex→4.6% of ethylene.

This amounts to 23% of incorporated 2-chloroethylphosphonic acid (2 moles/mole). By taking into consideration an incorporation rate of 2 moles of 2-chloroethylphosphonic acid per 1 mole of α-cyclodextrin, the yield obtained amounts to 80.2%, calculated for the theoretical value.

The X-ray diffraction powder diagram of α-cyclodextrin differs significantly from that of the complex of α-cyclodextrin and 2-chloroethylphosphonic acid. The diagram of α-cyclodextrin shows sharp reflection peaks at the values of 2θ°=11.7, 12.3, 13.5, 14.3, 21.8, while the diagram of the complex of α-cyclodextrin and 2-chloroethylphosphonic acid shows a significant reflection maximum only at 20°.

On taking the amount of the ethylene evolved in a Warburg apparatus as a function of time, the reaction velocity constants of first order, characteristic of the decomposition kinetics of 2-chloroethylphosphonic acid, can be calculated. This is illustrated in Table I. Table II shows that in a homogeneous aqueous solution cyclodextrin accelerates the formation of ethylene to a significant extent.

TABLE I

| t (°C.) | pH | k (minute$^{-1}$) |
|---|---|---|
| 27 | 6.64 | 9.2 × 10$^{-5}$ |
|  | 8.04 | 36.8 × 10$^{-5}$ |
|  | 11 | 138.2 × 10$^{-5}$ |
| 37 | 6.64 | 3.3 × 10$^{-4}$ |
|  | 8.04 | 13.8 × 10$^{-4}$ |
|  | 11 | 57.8 × 10$^{-4}$ |
| 47 | 6.64 | 1.4 × 10$^{-3}$ |
|  | 8.04 | 6.0 × 10$^{-3}$ |
|  | 11 | 24.4 × 10$^{-3}$ |

TABLE II

| t (°C.) | pH | α-CD-CEPA k (minute$^{-1}$) | CEPA k' minute$^{-1}$ | k/k' |
|---|---|---|---|---|
| 27 | 6.64 | 9.2 × 10$^{-5}$ | 7.6 × 10$^{-5}$ | 1.21 |
|  | 8.04 | 36.8 × 10$^{-5}$ | 26.9 × 10$^{-5}$ | 1.36 |
|  | 11 | 138.2 × 10$^{-5}$ | 86.0 × 10$^{-5}$ | 1.60 |

CEPA = 2-chloroethylphosphonic acid

EXAMPLE 2

Preparation of a complex of β-cyclodextrin and 2-chloroethylphosphonic acid

With β-cyclodextrin a 30% solution is prepared in distilled water under warming (80°–90° C.). A 40% 2-chloroethylphosphonic acid (Rol-Fruct, Chinoin product) solution of equal volume is added under vigorous stirring to the still warm solution. The solution thus obtained is cooled on an icecold waterbath under constant stirring and allowed to stand in a refrigerator overnight; the solution turns into a thick crystal-suspension. The precipitated complex is filtered off under cooling, washed with cold mother-liquor and dried in a vacuum desiccator over potassium hydroxide. The drying requires two or three days and can be accelerated by comminution. A greenish product is obtained which can be readily pulverized and in powdered form is white small crystals. Yield: 60–70%, calculated for the introduced β-cyclodextrin.

The 2-chloroethylphosphonic acid content of the β-cyclodextrin-2-chloroethylphosphonic acid complex thus obtained is determined by measuring the argentometric chloride content according to Volhard and the amount of the ethylene formed by decomposition of the complex (according to Warburg). The aqueous solution of the complex is free of chloride ions (according to Volhard); the fixed chlorine content of the 2-chloroethylphosphonic acid is determined according to Volhard by heating to boiling with a 1 N potassium hydroxide solution for 15 minutes. 3-% chlorine→2.4% of ethylene→12% of 2-chloro ethyl phosphonic acid→1.15 moles of 2-chloro ethyl phosphonic acid per 1 mole of β-cyclodextrin. The amount of ethylene formed by decomposition also corresponds to an incorporation rate of 1.2 moles of 2-chloroethylphosphonic acid per 1 mole of β-cyclodextrin.

EXAMPLE 3

Preparation of a complex of γ-cyclodextrin and 2-chloroethylphosphonic acid

To a 30% warm (70°–80° C.) aqueous solution of γ-cyclodextrin a 40% solution of 2-chloroethylphosphonic acid (Rol-Fruct, Chinoin product) of equal volume is added under stirring in an analogous manner to the preceding Examples. The clear solution thus obtained is cooled in icecold water and allowed to stand in a refrigerator overnight. The precipitated product is filtered off and dried in a vacuum desiccator for 2 days. The dry product is of a greenish shade and pulverized form is of white powder crystals. Yield: 65%, related to the introduced γ-cyclodextrin. The product is the complex of γ-cyclodextrin and 2-chloroethylphosphonic acid. 2-chloro ethyl phosphonic acid content:

Free chloride content according to Volhard: 0%. Fixed chloride content according to Volhard, after heating to boiling with potassium hydroxide for an hour: 5.3 of Cl→4.3% of ethylene→21.2% of 2-chloroethylphosphonic acid→incorporation rate of 2.4 moles/mole.

EXAMPLE 4

A crude cyclodextrin conversion mixture is prepared from starch in a known manner by using a cyclodextrin transglucosilase enzyme obtained by culturing *Bacillus macerans*.

The crude conversion mixture thus obtained contains about 40–80% of partially decomposed starch, linear dextrins, 38–42% of $\beta$-cyclodextrin, 2–10% of $\alpha$-cyclodextrin and 4–10% of $\gamma$-cyclodextrin. The average composition of the mixture is such that beside 6 parts of $\beta$-cyclodextrin 2 parts of $\alpha$-cyclodextrin and 2 parts of $\gamma$-cyclodextrin are formed.

The 2-chloroethylphosphonic acid complex is prepared from the crude conversion mixture thus obtained by forming at 50° C. a 30% aqueous solution from the conversion mixture and adding thereto a 40% aqueous solution of 2-chloroethylphosphonic acid; the amount of the 2-chloroethylphosphonic acid thus added corresponds to 20–30%, calculated for the total cyclodextrin content. The mixture is allowed to stand in a refrigerator overnight and worked up as described in the preceding Examples. The complex of 2-chloroethylphosphonic acid formed with the various cyclodextrins precipitates together with a part of the linear dextrins. The 2-chloroethylphosphonic acid content of the product amounts to 18%.

EXAMPLE 5

The partially decomposed starch and linear dextrins formed in the course of the manufacture of $\beta$-cyclodextrin are removed by precipitation. The residue is subjected to crystallization; the mother-liquor of the first crystallization batch contains $\alpha$-, $\beta$- and $\gamma$-cyclodextrins approximately in equal amounts. This product was hitherto a discarded waste material. According to the present invention, however, it can be utilized for the preparation of an inclusion complex of 2-chloroethylphosphonic acid and cyclodextrin.

The mother-liquor obtained by the first crystallization of $\beta$-cyclodextrin is evaporated in vacuo to a solid substance content of 20%. To 100 l. of the concentrated mother-liquor 15 l. of a 2-chloroethylphosphonic acid solution (dry substance content 40% by weight) are added. The mixture is cooled under stirring, and allowed to stand overnight. The precipitated product is filtered off and dried. Thus 21 kg. of a white powder-like product are obtained; 2-chloroethylphosphonic acid content 20.2%.

EXAMPLE 6

Acceleration of the ripening of red pepper by means of a complex of ethrel and cyclodextrin The complex of ethrel and cyclodextrin can be successfully used for the acceleration of the ripening of red pepper as a result of the fact that by a slow and long-lasting evolution of ethylene the complex ensures the harmony of the economical and biological value of the product in the course of ripening. When ethylene is used for the acceleration of ripening, the biological properties (coloration, germinating power) often fall behind to a certain extent. This undesired side effect can be diminished by the use of the new complex of the present invention and this is accompanied by an improved acceleration of ripening.

|  | Stain (pigment) content % |
|---|---|
| 3 l/ha ethrel | 86 |
| 3 l/ha of an ethrel-cyclodextrin complex | 120 |

A further advantage is that the use of the ethrel-cyclodextrin complex of the present invention brings about savings with respect to the active ingredient. Furthermore the direct beneficial effect of cyclodextrin prevails in the increase of the amount of crops.

EXAMPLE 7

Regulation of germination of coated celery seeds with a complex of ethrel and cyclodextrin The complex can be preferably used—either alone or together with other plant growth regulators—for the stimulation of germination and increase of the percental germination of coated celery seeds having a low germinating-power and also for the formation of a uniform plant stand. Celery seeds are coated by admixing the same with about 0.5% of an ethrel-cyclodextrin complex according to the present invention in a conventional dragee pan. The thus coated seeds can be stored under suitable circumstances for several months without any decrease of the ethylene evolution. A further advantage of the use of the complex for coating the seeds is that, contrary to the use of ethrel carried out at lower pH values, it does not corrode the apparatus.

It is known from prior art (T. H. THOMAS—N. L. BIDDINGTON—D. PALEVICH: Improving the performance of pelleted celery seeds with growth regulator treatments, Acta Hort. Tech. Commun, ISHS., The Hague, 1978, 83:235-243) that the germination of celery seeds can be hastened by a combined treatment carried out with several growth hormones. These procedures involving the usual drenching accomplished with gibberellinic acid and ethrel for 48 hours, drying and subsequent coating in a dragee pan are circumferential and time consuming.

On the other hand the use of the complex of the present invention (addition of the complex to the coating material, coating of the seed, and subsequent germination of the coated seed in a solution of gibberellinic acid) makes the process much simpler.

EXAMPLE 8(a)

Celery seeds coated with a complex of ethrel and cyclodextrin are germinated in a 100 ppm aqueous solution of gibberellinic acid in a Petri dish in the dark at 25° C. The germinating power and germination % data obtained are summarized in the following Table.

|  | number of days | | |
|---|---|---|---|
|  | 8 | 12 | 20 |
| bare celery seed | — | — | — |
| bare celery seed + gibberellinic acid | 60 | 60 | 60 |
| normal celery dragee | — | — | — |
| normal celery dragee + gibberellinic acid | — | — | — |
| celery dragee coated with a complex of ethrel and cyclodextrin | — | — | — |
| celery dragee coated with a complex of ethrel and cyclodextrin and treated with gibberellinic acid | 10 | 20 | 20 |

EXAMPLE 8(b)

Celery seeds coated with a complex of ethrel and cyclodextrin are dried in a vacuum drying oven at 100° C. whereby the dragee loses 50% of its usual water content. The dragees thus treated are germinated in a Petri dish, at 25° C., in the dark, in a 100 ppm aqueous gibberellinic acid solution. Thus the germination % and germinating power can be improved.

|  | number of days | | |
| --- | --- | --- | --- |
|  | 8 | 12 | 20 |
| ethrel-cyclodextrin dragee, without drying + gibberellinic acid | 10 | 20 | 20 |
| ethrel-cyclodextrin dragee, dried at 100° C. + gibberellinic acid | 10 | 40 | 40 |

The following biological tests are carried out for the determination of the ethylene effect of a complex of 2-chloroethylphosphonic acid and cyclodextrin (referred to as the complex):

(1) The endogenic ethylene production of the plant tissues is measured by our published method (Mrs. Tetenyi, Bot. Közl. 62:2, 89–94, 1977). Seeds of Pisum sativum L. cv (Rajna dwarf) disinfected with hydrogen peroxide are germinated in the dark at 27° C. for 48 hours. For the test acotyledonous hypocotyds are isolated, and ten of them are placed into a phial containing a wet filter-paper strip and the plant to be tested. The phials are closed twice with rubber caps and 1 ml samples of the gaseous ethylene formed in this closed area within 24 hours are directly injected into a gas chromatograph.

The measurements are carried out in a Jeol 810 type gas chromatograph equipped with a flame ionization detector. The following parameters are used: size of the column:diameter 3 mm., height 3 m., glas, the column is filled with 10% DEGS, Chrom W, 60/80 mesh. Temperature: 50° C. in the column, 130° C. in the injection block; 100° C. at the detector. Carrier gas: $N_2$, velocity: 20 ml./min. The gaseous ethylene evolved in the plant is identified and measured with the aid of an ethylene standard obtained from a flask from which a calibration curve is prepared.

Samples pre-treated by three different methods are used for the test: The control germs are directly placed into the dishes without any treatment (A). Other germs are rolled in the crystals of the complex and are put into the dishes together with the substance adhered thereto (B). The third samples are the crystals of the complex adhered to the wet filter-paper (C).

Only the gas sample taken from the air-space of germs treated with the complex powder gave an ethylene peak (38–40 $C_2H_2$/10 germs, 24 hours). This proves that the complex penetrated into the living tissues in solid or dissolved form or as the solution of the liberated 2-chloroethylphosphonic acid and in the tissues under the physiological conditions at the given pH value ethylene was formed.

(2) One of the most characteristic ethylene effects exerted on plants is abscission. The following abscission test is carried out: Phaseolus vulgaris L. cv. "Juliska" bean plants are cultivated in a phytobox under standard conditions (Flar Floralux Fx fluorescent lamp, 4000 lux, photoperiod 12 hours) in 10×10 cm. plastic vessels (three plants in a vessel). The plants are decapitated, whereupon the primary foliage leafs standing on the roots are dusted with the complex. Thus the surface of the leaf contains as much active ingredient as adhered thereto. As control plants having a primary foliage leaf and immersed in water (untreated) or into a 2-CEPA solution are used. The plants are then kept in the phytobox. After 36 hours only the plants treated with the complex show a 100% abscission. The leaves of the control plants do not fall.

The above data show that the complex in some way penetrated the surface of the leaf and even translocated in the suitable part of the plant (leaf-stalk) and the ethylene set free in the tissues at the pH of the cells induced the abscission.

In the case of the control test carried out with a plant immersed into a solution of 2-CEPA no abscission was found. This shows that dusting carried out with the complex of the present invention results in a higher ethylene effect than that which can be applied onto the leaves by immersing in the solution and one application. (It is to be noted that the concentration of $10^{-2}$ of the 2-CEPA-solution used is the highest concentration still not injuring the tissues of the leaves).

We claim:

1. An inclusion complex of 2-chloroethylphosphonic acid formed with $\alpha$-, $\beta$- and/or $\gamma$-cyclodextrin.

2. An inclusion complex of 2-chloroethylphosphonic acid and $\alpha$-cyclodextrin containing 10 to 30% by weight of 2-chloroethylphosphonic acid.

3. An inclusion complex of 2-chloroethylphosphonic acid and $\beta$-cyclodextrin containing 10 to 30% of 2-chloroethylphosphonic acid.

4. An inclusion complex of 2-chloroethylphosphonic acid and $\gamma$-cyclodextrin containing 10 to 30% by weight of 2-chloroethylphosphonic acid.

5. A process for the preparation of crystalline inclusion complexes of 2-chloroethylphosphonic acid which comprises reacting 2-chloroethylphosphonic acid with $\alpha$-, $\beta$- and/or $\gamma$-cyclodextrin or a mixture of one or more of the said cyclodextrins formed with linear dextrins and/or partially decomposed starch.

6. A process according to claim 5 which comprises adding an aqueous solution of 2-chloroethylphosphonic acid to cyclodextrins or a mixture of cyclodextrins and linear dextrins or to an aqueous solution thereof.

7. A process according to claim 5 which comprises adding a solution of 2-chloro ethyl phosphonic acid in a mixture of water and a water-miscible organic solvent to cyclodextrins or a mixture of cyclodextrins and linear dextrins or an aqueous solution thereof.

8. A process according to claim 7 which comprises using lower alcohols and/or ketones as solvent.

9. A plant growth regulating composition comprising as active ingredient an inclusion complex of $\alpha$-, $\beta$- and/or $\gamma$-cyclodextrin and 2-chloroethylphosphonic acid containing 10 to 30% by weight of 2-chloroethylphosphonic acid, and water as diluent.

10. A plant growth regulating method which comprises using as active ingredient an inclusion complex of 2-chloroethylphosphonic acid formed with an $\alpha$-, $\beta$- and/or $\gamma$-cyclodextrin.

* * * * *